United States Patent [19]
Ganzler et al.

[11] 3,981,908
[45] Sept. 21, 1976

[54] PREPARATION OF GLYCOL ESTERS

[75] Inventors: Wolfgang Ganzler, Darmstadt-Arheilgen; Klaus Kabs, Seeheim; Gunter Schröeder, Ober-Ramstadt, Darmstadt, all of Germany

[73] Assignee: Röhm GmbH, Darmstadt, Germany

[22] Filed: Sept. 30, 1974

[21] Appl. No.: 510,613

[30] Foreign Application Priority Data
Nov. 12, 1973 Germany.......................... 2356389

[52] U.S. Cl............................................ 260/497 R
[51] Int. Cl.².......................................... C07D 67/05
[58] Field of Search ................................ 260/497 R

[56] References Cited
UNITED STATES PATENTS
3,255,238  6/1966  Roeler............................ 260/497 R

OTHER PUBLICATIONS

Roberts et al., *Basic Principles of Organic Chemistry*, (1965), pp. 365–366, 1209–1210 and 1226–1227.

*Primary Examiner*—Lorraine A. Weinberger
*Assistant Examiner*—Michael Shippen
*Attorney, Agent, or Firm*—Curtis, Morris & Safford

[57] ABSTRACT

An improved process for preparing glycol esters by reacting an olefin with oxygen in the presence of a carboxylic acid or an inert medium containing a carboxylic acid is described in which the improvement comprises carrying out the reaction in the presence of a composite catalyst composed of or containing A. a compound of boron, aluminum, silicon, phosphorus or a combination thereof, and B. a compound of iron, copper or a combination thereof.

7 Claims, No Drawings

PREPARATION OF GLYCOL ESTERS

This invention relates to an improved process for the preparation of glycol esters by oxidation of an olefin with oxygen an a carboxylic acid in the presence of new composite catalyst.

Processes for reacting olefins with molar oxygen in carboxylic acid to the corresponding glycol mono- or di-esters in the presence of catalysts have already been known for some time. French Patent No. 1,421,288 (1965) describes the use of a metal salt, e.g. a cobalt, manganese or vanadium acetate, naphthenate, stearate or chloride, if desired in conjunction with a bromide, as oxidation catalyst. British Patent No. 1,124,862 describes the promotion of the reaction with a palladous salt and either a nitrate or nitrite. According to French Patent No. 1,419,966, the salts of noble metals of Group VIII of the Periodic System, specifically palladium acetate, are good catalysts for the oxidation of an olefin in glacial acetic acid; in this process nitric acid and nitrates are also used as oxidizing agents. U.S. Pat. No. 3,542,857 describes a process for preparing glycol esters from olefins and molecular oxygen in a carboxylic acid by use of a cerium salt as catalyst which is soluble in the carboxylic acid. In German Offenlegungsschrift No. 1,931,563 the preparation of glycol esters from an olefin and oxygen in the presence of a carboxylic acid is described in which the catalyst is iodine or an iodide together with at least one alkali metal cation, nitrogen cation or cation of a heavy metal of Atomic Numbers 21–30 or 48 of the Periodic System. Essentially the same process is described in German Offenlegungsschrift No. 1,948,787 with a catalyst system composed of bromine, chlorine or a bromine- or chlorine-containing compound on the one hand and a cation of a metal having several valencies such as tellurium, cerium arsenic, antimony, manganese or cobalt. German Offenlegungsschrift No. 2,126,505 also suggests the use of metal cations of variable valence, i.e. tellurium, cerium, antimony, manganese, vanadium, gallium, arsenic, cobalt, copper, selenium, chromium and silver in combination with bromine, chlorine, hydrobromic acid or hydrochloric acid as catalysts in the preparation of glycol esters from olefins, oxygen and a carboxylic acid. Finally, British Patent No. 1,058,995 describes the same process in which active catalysts are a palladium-II salt, an acetate of an alkali metal, and alkaline earth metal, copper, iron, tin or nickel, and a halide of any of these afore-named metals.

The selectivity of the known catalysts and/or the yields attained with them are not entirely satisfactory. In addition, it is to be noted that catalytic systems containing a platinum metal require steps for reclaiming the used catalyst.

It has now been found that composite catalysts, which in part are of boron, aluminum, silicon and/or phosphorus and in part of copper and/or iron, preferably in the form of salts, permit the reaction of an olefin with oxygen and a carboxylic acid to form glycol esters to proceed with higher selectivity and outstandingly good yields. The process can be carried out batch-wise or continuously and the oxygen can be utilized as molecular oxygen or in the presence of a comparatively large proportion of inert gas, e.g., in the form of air.

It is surmised that the catalysts of the invention are complex, possibly multi-nuclear compounds. However this assumption is not definitely established. The invention is, therefore, not to be limited by any theory of operation expressed herein, but is illustrated and exemplified by the description of the components that are operable in the reaction medium to result in the desirable preparation of glycol esters in high yields and excellent selectivity.

It is preferred, in accordance with the present invention, that at least one of the elements in the composite catalyst be in the form of a halide. To the extent that the named metals are used in form in which they are soluble in the reaction medium, e.g., as acetates or acetyl acetonates, the catalytic activity-promoting halide can be introduced into the reaction mixture in the form of a halide of another metal, preferably as an alkali metal halide.

The process can be carried out under conditions that have heretofore been proposed and utilized, i.e. at elevated temperatures, preferably within the range of about 50° to about 200°C. Lower or higher temperatures can, however, be used, bearing in mind that the result will be a loss of speed of reaction in one instance and more severe demands on the apparatus in other instance.

In order to obtain satisfactory conversions and yields, it is advantageous to carry out the process at elevated pressure. When the process is carried out batchwise, the minimum pressure to be applied is more or less dependent on the amount or concentration of olefin and oxygen to be introduced into the reaction medium as well as by the temperature to be employed.

While it is generally preferred to use, as a reaction medium, the carboxylic acid which is also involved in the esterification reaction, it is also within the scope of the invention and may be advantageous in certain instances to utilize as solvent or co-solvent an inert liquid such as benzene, toluene or xylene. The final glycol ester may itself be utilized as such an inert solvent.

The glycol esters prepared in accordance with the improved process of the invention have a wide range of utilities that are known in the art, e.g. as solvents and softening agents. Glycol esters of higher carboxylic acids are useful in the industry as surface active agents. Inasmuch as the hydrolysis of glycol esters is well known to be a simple and easily performed reaction, the process of the invention is also eminently useful for the preparation of glycols in which the hydrolytically split off acid, possibly after concentration, is recycled to the ester-forming process.

The following examples illustrate the invention without being intended to limit the scope of applicant's invention specifically to the reactants or process described. In each of these examples, the procedure was to introduce into a Teflon-coated autoclave a reaction medium consisting of acetic acid as the solvent, acetic anhydride as a water-binding agent, and the composite catalyst. Thereafter the autoclave was closed, the olefin reactant and oxygen of air were introduced under pressure, and the autoclave was heated to approximately 150°C. When propylene was used as the reactant, it was introduced under a liquifying pressure of approximately 10 atmospheres in order to achieve saturation of the reaction medium with this olefin. Conversion temperature being reached, the reaction occurs within a few minutes.

EXAMPLE 1

Boron chloride diacetyl acetonate was prepared from boron trichloride and acetyl acetone as described in Liebig's Ann. Chem. 344,326 (1905). 2 g of this were dissolved together with 2 g of cupric chloride in 500 ml of glacial acetic acid and 50 ml acetic anhydride and saturated with propylene. Then oxygen was introduced under a pressure of 20 atmospheres and the contents heated to 150°C.

Distillation of the products resulted in a yield of 37.9 g propylene glycol diacetate.

EXAMPLE 2

Propylene and oxygen were introduced, in the manner described in Example 1, into a solution of 500 ml glacial acetic acid and 50 ml acetic anhydride containing 2 g aluminum acetate and 2 g cupric chloride. The contents were then heated to approximately 150°C. After cooling and release of pressure, the contents were subjected to distillation. 30.6 g propylene glycol diacetate were obtained.

EXAMPLE 3

A complex salt was prepared from 1.7 g silicon tetrachloride, 3.0 g acetyl acetone and 1.9 g ferric chloride in 25 m. glacial acetic acid. The resulting precipitate was filtered off under suction and dissolved in 500 ml glacial acetic acid and 50 ml acetic anhydride. The resulting solution was then saturated with propylene and with oxygen at 20 atmospheres pressure, and subjected to the conditions described in Example 1. The distillation of the reaction product resulted in a yield of 8.5 g propylene glycol diacetate.

EXAMPLE 4

2 g silicon tetrachloride were dissolved together with 2 g cuprous chloride and 2 g cupric chloride in 500 ml glacial acetic acid and 50 ml acetic anhydride. This solution was saturated with propylene and with compressed air at 40 atmospheres, and then heated to 160°C. Distillation resulted in the preparation of 4.6 g propylene glycol diacetate.

EXAMPLE 5

2 g phosphorus trichloride and 2 g phosphorus pentachloride were dissolved with 2 g cupric chloride in 500 ml glacial acetic acid and 50 ml acetic anhydride and then further treated a described in Example 4. 5.2 g propylene glycol diacetate were obtained.

We claim:

1. In a process for preparing glycol esters in a liquid phase by the reaction of an olefin with oxygen and a carboxylic acid, the improvement wherein the reaction is carried out at a temperature from about 50° to 200°C. in the presence of a catalyst consisting essentially of:
   A. a member selected from the group consisting of compounds of boron, aluminum, silicon, and phosphorus which are soluble in the liquid reaction medium, and
   B. a member selected from the group consisting of compounds of iron and copper which are soluble in the liquid reaction medium,
   at least one of the catalyst components being a halide.

2. The process defined in claim 1 which the catalyst consists essentially of boron chloride diacetyl acetonate and cupric chloride.

3. The process defined in claim 1 in which the catalyst consists essentially of aluminum acetate and cupric chloride.

4. The process defined in claim 1 in which the catalyst is a complex salt of silicon tetrachloride, acetyl acetone and ferric chloride.

5. The process defined in claim 1 in which the catalyst consists essentially of silicon tetrachloride, cuprous chloride and cupric chloride.

6. The process defined in claim 1 in which the catalyst consists essentially of phosphorus trichloride, phosphorus pentachloride and cupric chloride.

7. The process defined in claim 1 in which the reaction is carried out at an elevated pressure within the range of from about 10 to 75 atmospheres.

* * * * *